(12) United States Patent
Boyd

(10) Patent No.: US 6,231,337 B1
(45) Date of Patent: May 15, 2001

(54) DENTAL MOUTHPIECE AND METHOD OF MAKING SAME

(76) Inventor: James P. Boyd, 710 Midori Ct., Solana Beach, CA (US) 92075

( * ) Notice: Subject to any disclaimer, the term of this patent is extended or adjusted under 35 U.S.C. 154(b) by 0 days.

(21) Appl. No.: 09/490,107

(22) Filed: Jan. 24, 2000

(51) Int. Cl.$^7$ .................................................. A61C 13/00
(52) U.S. Cl. ............................................................ 433/6
(58) Field of Search ............................................ 433/6, 71

(56) References Cited

U.S. PATENT DOCUMENTS

| | | | |
|---|---|---|---|
| 4,624,640 | * | 11/1986 | Tesini ...................................... 433/71 |
| 4,892,478 | * | 1/1990 | Tateosian et al. ......................... 433/6 |
| 5,031,611 | * | 7/1991 | Moles ........................................ 433/6 |
| 5,503,552 | * | 4/1996 | Diesso ...................................... 433/71 |
| 5,554,665 | * | 9/1996 | Tateosian et al. ....................... 522/30 |
| 5,779,470 | * | 7/1998 | Kussick ..................................... 433/6 |
| 5,885,073 | * | 3/1999 | Kussick ..................................... 433/6 |

* cited by examiner

Primary Examiner—Todd E. Manahan
(74) Attorney, Agent, or Firm—Donn K. Harms

(57) ABSTRACT

A method of making an occlusally retained mouthpiece. A mouthpiece substrate is coated with a resin precursor that is neither caustic nor irritating to teeth or gingival tissue. The resin precursor is curable to form a resin selected from the group consisting of Bisphenol A diglycidyl ether dimethacrylate and urethane dimethacrylate. The substrate is pressed against teeth with the teeth pressed into the resin coating. When the resin is partially cured to a shape retaining state, it is removed from the teeth and curing is completed to form a tough flexible material. Alternatively, the substrate may be held against the teeth and the resin precursor may be applied along the teeth-substrate interface with a mixing syringe. High intensity light may be used to cure the resin or enhance catalytic curing. For best results the substrate is made from the same material as is applied to the teeth.

14 Claims, 1 Drawing Sheet

DENTAL MOUTHPIECE AND METHOD OF MAKING SAME

FIELD OF THE INVENTION

This invention relates to dental devices comprising a shaped member for mounting on the teeth with a hardenable molding composition. These devices may, for example, treat symptoms of temporomandibular and bruxism disorders or facilitate mandibular advancement and breathing enhancement.

BACKGROUND OF THE INVENTION

A variety of occlusally retained mouthpieces have been developed by dentists for a number of different purposes. These mouthpieces are assembled and fitted to the teeth in several different ways.

There are two basic methods for fabricating an intraoral occlusally retained mouthpiece, either forming the mouthpiece directly on the teeth or indirectly on a model of the teeth.

Indirect methods typically require the dentist to take impression of the teeth from which plaster models are fabricated. These models are then used to make the mouthpiece in a laboratory setting. The increased cost and time delay to the patient in acquiring such a mouthpiece has influenced dentists to pursue direct intraoral methods of fabrication.

When fabricating a mouthpiece directly, conventionally an ethyl or methyl methacrylate acrylic resin is used. When cured in the laboratory, these acrylics are safe, but when cured directly in a patient's mouth they can be highly irritating and caustic. In addition they may burn the gingival tissue due to the heat generated during curing. Further, such use of acrylics is contraindicated when the patient is pregnant.

To directly fabricate such a mouthpiece, typically the dentist either forms a doughy "rope" of acrylic to be molded onto the teeth during the curing state. The rope is placed on a plastic substrate, pressed against the teeth and cured. The acrylic monomer slightly dissolves the surface of the substrate so that when fully cured a seamless and permanent bond is formed between the shaped acrylic and the substrate.

Other resins, such as thermoplastic resins like ethylene vinyl acetate, are sometimes used. However, these must be softened by heat which may have deleterious effects on the teeth and gums. Other resins generally do not bond well to the plastic substrates used in such mouthpieces. If the bond breaks while the device is in use, choking on the separated parts is possible.

Typical of the indirect fabrication method is that described by Thornton in U.S. Pat. No. 5,755,219. To produce a device for improving breathing, two trays are provided. The trays are filled with an ethylene vinyl acetate precursor, heated to about 150° F. and pressed against the upper and lower teeth and the resin is cured. This resin at this high temperature may cause discomfort and injure the gingival tissue.

A mouthpiece or splint intended to treat conditions such as temporomandibular joint disorder is described by Summer in U.S. Pat. No. 5,173,048. An arch is held to the lower teeth by metal clips and is coated on the upper surface with an uncured dental acrylic. The patient bites against the arch, embedding the upper teeth in the acrylic, which is then cured. The acrylic is likely to provide the problems detailed above.

A dental device for snoring and sleep apnea treatment is described by Kidd et al. in U.S. Pat. No. 5,829,441. Arch trays are filled with a thermoplastic material, such as ethylene vinyl acetate. The trays is heated to about 165 to 185° F., placed in the patient's mouth. The patient bites into the material in the trays and waits for the material to cool and harden. The heat from the material is likely to have negative effects on the teeth and gum tissue.

Thus, there is a continuing need for improved dental mouthpiece material that are not toxic or irritating to the teeth or gums, do not contain harmful chemicals that irritate the gingival tissue or produce fumes or require heat that are disturbing and potentially harmful to the patient, will bond well with convenient substrate materials and may be removed from the teeth while still quite flexible but shape retaining to allow undercuts and the like to be cleaned up prior to full cure to a tough but slightly flexible state.

SUMMARY OF THE INVENTION

The above-noted problems, and others, are overcome in accordance with this invention by a method of forming mouthpieces and the like which comprises the steps of providing a dental substrate adapted to being brought into contact with the teeth and a curable resin precursor; namely a Bisphenol-A diglycidyl ether dimethacrylate ($BIS_{13}$ GMA) resin or a urethane dimethacrylate (UDMA) resin (or mixtures of these resins) which is neither caustic nor irritating to teeth or gingival tissue, applying a quantity of the resin precursor to a mouthpiece substrate, inserting the coated substrate into the patient's mouth and into contact with at least one tooth, partially curing the resin precursor to a flexible, shape retaining state, removing the substrate from the patient's mouth, fully curing the resin to a tough, slightly flexible, state and removing any excess resin from interproximal and undercut areas to make the resulting mouthpiece easy to insert and remove from the mouth.

The resin precursor may be cured by either catalytic means, by high intensity light or a combination thereof. For catalytic curing, the resin precursor is mixed with a catalyst, typically a peroxide. For light curing, a conventional light activating initiator is mixed with the resin precursor. The resin precursor and curing agent can be mechanical mixed and applied or can be mixed though simultaneous application with a dual syringe. The mixture may be applied to a surface of the substrate, with the coated substrate then pressed against the teeth. Or, the substrate may be inserted first and held in place (typically clamped between upper and lower teeth and the mixture applied along the tooth-substrate interface.

BIS-GMA and UDMA will not bond to the conventional dental mouthpiece substrate materials used with acrylic impression material. Therefore, a substrate resin must be selected that will bond. For optimum results, the mouthpiece substrate is formed from the same resin precursor as is applied to the teeth. These resins are entirely non-toxic and non-irritating, will cure to an intermediate, relatively flexible state allowing easy withdrawal from the teeth, then will complete the cure outside the mouth to a tough but somewhat flexible state, ideal for ease of use of the mouthpiece.

These BIS-GMA and UDMA resins have been used for sometime for filling pits, fissures and cavities in teeth, bonding ceramic veneer to teeth and surface restoration of front teeth, etc. They bond very firmly to tooth surfaces and resist wear and breaking when all water has been removed from the tooth surface and the surface has been etched or otherwise treated.

Surprisingly, I have found that these resins will not bond to tooth surfaces if no (or very little) filler is used and if the partially cured resin impression is removed from the mouth while still in a highly flexible state. The normal thin film of water on the teeth also allows release the partially cured resin from the teeth. The prior art involving dental uses for these resins stress the need for drying and treating the teeth, thus pointing away from the use in mouthpieces as claimed in this application.

Typical of BIS-GMA resins that can be cured by a catalyst or high intensity light is that available under the Dual Cure trademark from Nulite Systems International. Typical UDMA resins include Megabond from the Harvey J. Bosworth Company, Prisma VLC Dycal baseline composition and Dyract resin restorative system from Dentsply, and Seal-Rite UDMA pit and fissure sealant from Pulpdent Corporation. They are always filled with hard filler particles such as silica, aluminum, zinc, tin, copper and/or iron to give them the desired color and necessary hardness for long useful life on the teeth. While sold for use with dry, treated, teeth to bond to the teeth, they are highly effective in the manufacture of various mouthpieces in accordance with the methods of this invention.

The mouthpieces made by the method of this invention have a wide variety of uses, such as protective device for treating bruxism, jaw-advancement devices for joint-joint conditions or snoring, a splinting device for loose teeth, a device for breaking habits such as thumb sucking or tongue-thrusting, etc.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
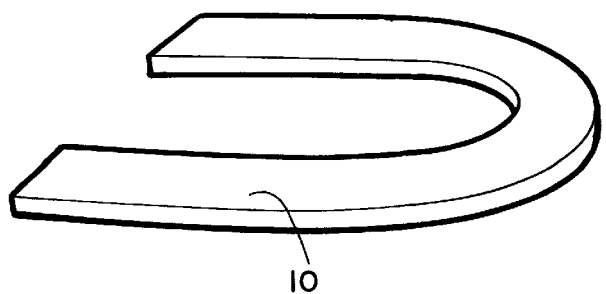
FIG. 1 is a perspective schematic view of a dental substrate.

Referring to FIG. 1, there is seen an arch-shaped mouthpiece substrate 10. The material of substrate 10 is fabricated from is selected to be fully compatible with the resins applied thereto, as detailed below. The shape accords with the layout of teeth in a patient's mouth. A simple arch is shown for clarity. Any other substrate shape may be used if desired, such as tray shapes, trough shapes, rectangular shapes for engaging only a few teeth or the discluder shape shown in my previous patent, U.S. Pat. No. 5,499,633.

Figure 2:
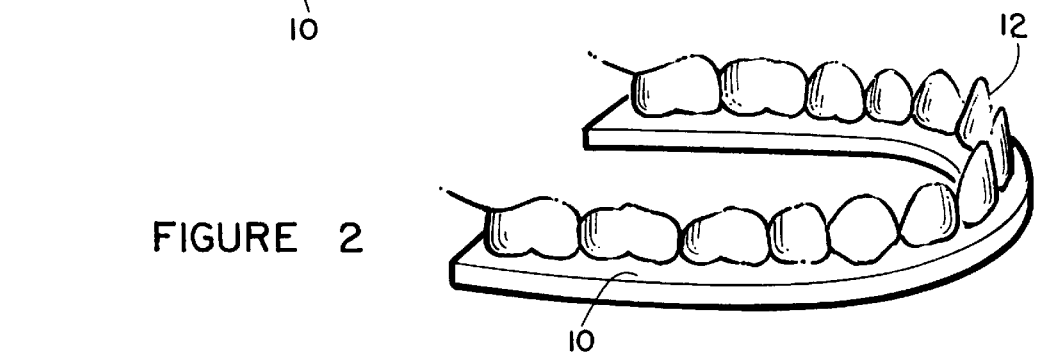
FIG. 2 is a perspective view of the substrate of FIG. 1 in contact with the upper teeth, with the gums, etc. omitted for clarity of illustration.

FIG. 2 shows substrate 10 of FIG. 1 in contact with a patient's upper teeth 12. Details of gums, lips, etc. are omitted for clarity of illustration. Substrate 10 will not directly contact all teeth, since the tips of the teeth will generally not all be in a single plane.

Figure 3:
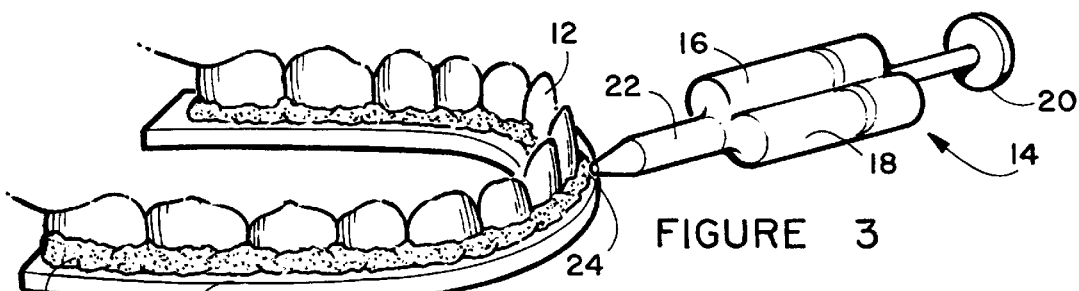
FIG. 3 is a perspective view illustrating one method of applying impression resin to the teeth and substrate.

FIG. 3 shows one method of applying the resin precursor and catalyst to the interface of substrate 10 and teeth 12. Here a mixing syringe 14 that contains the BIS-DMA or UDMA resin precursor in one chamber 16 and the catalyst in the other chamber 18. Equal amounts of each ingredient will be forced by pressing plunger 20 to force the ingredients into mixing section 22 which has vanes or the like to mix the two ingredients together as they pass through and are expelled through nozzle 24. Mixture 26 is applied to any suitable thickness along the top surface of substrate 10 and up the sides of teeth 12.

Figure 4:
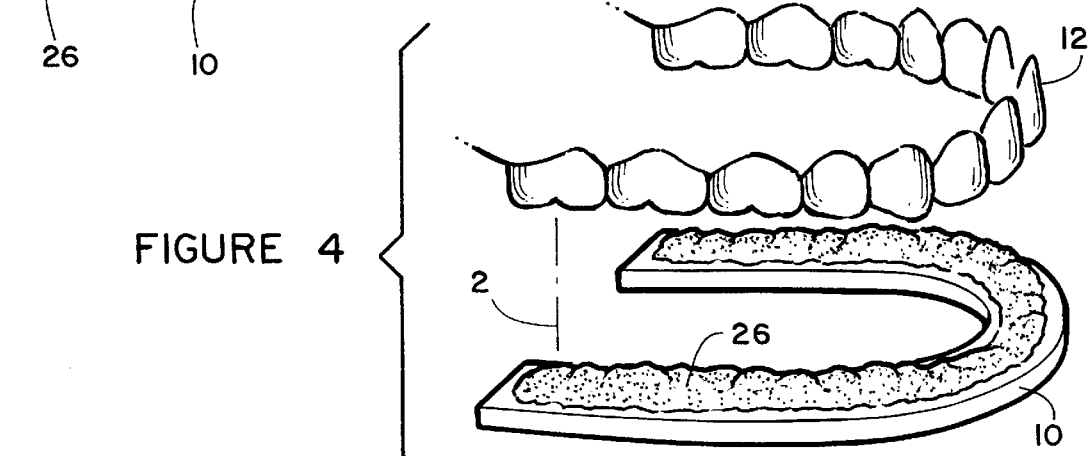
FIG. 4 is an exploded perspective view of a second method of applying impression resin to the teeth and substrate.

FIG. 4 illustrates a second method of applying resin mixture 26 and obtaining the tooth impression. Here the resin mixture 26 is applied to substrate 10 to form a layer of predetermined thickness. The coated substrate then is brought into contact with teeth 12 as indicated by arrow 28 and held in place by the patient bringing his teeth together or any other suitable means.

Figure 5:
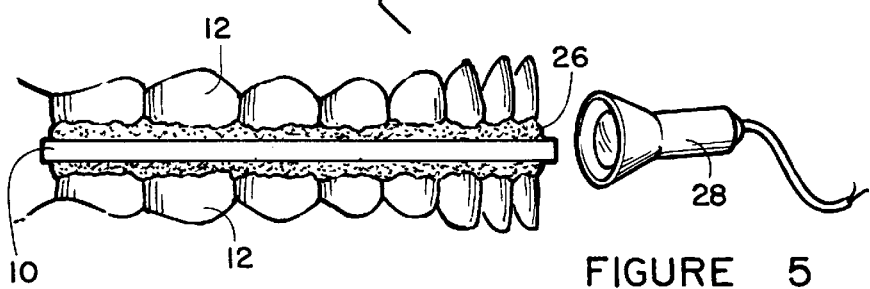
FIG. 5 is a side elevation view illustrating the application of impression resin to both sides of a substrate to engage both upper and lower teeth.

FIG. 5 shows the application of the BIS-GMA or UDMA resin mixture 26 to both sides of substrate 10. Typically, substrate 10 is placed between the upper and lower teeth and held in place by light clamping pressure between the teeth. The resin mixture is applied by a syringe 14 as shown in FIG. 3 or by the pre-application of the mixture to substrate 10 as seen in FIG. 4.

Where the resin is light activated, or where light activation is to be used in conjunction with a catalyzed resin, a high intensity light source 28 may be positioned as shown in FIG. 5 and moved along the mixture to initiate or aid in curing.

The resin is partially cured while in contact with the teeth to a shape retaining but very flexible state. Substrate 10 with the partially cured resin 26 bonded thereto is removed from the mouth. Any undercuts can be trimmed away and curing completed, though the passage of time in the case of the catalyzed resin or by the application of further high intensity light.

While certain specific relationships, materials and other parameters have been detailed in the above description of preferred embodiments, those can be varied, where suitable, with similar results. Other applications, variation and ramifications of the present invention will occur to those skilled in the art upon reading the present disclosure. Those are intended to be included within the scope of this invention as defined in the appended claims.

I claim:

1. A method of making an occlusally retained mouthpiece which comprises the steps of:

providing a substrate;

providing a two-part catalytically cured resin precursor which is neither caustic nor irritating to teeth or gingival tissue;

said substrate formed from a resin selected from the group consisting of Bisphenol A dialycidyl ether dimethacrylate and urethane dimethacrylate resins and mixtures thereof;

said resin precursor being selected from the group consisting of precursors for Bisphenol A diglycidyl ether dimethacrylate and urethane dimethacrylate resins and mixtures thereof;

applying a quantity of a mixture of said resin precursor and a catalyst therefor to said substrate;

inserting said substrate into a patient's mouth;

bringing upper and lower teeth into contact with said substrate pressing said substrate against at least one tooth so that said at least one tooth is embedded into said mixture;

partially curing said resin precursor to a shape retaining resin state;

removing said substrate from said patient's mouth;

fully curing said resin to a tough, flexible state bonded to said substrate; and removing any excess resin from interproximal and undercut areas to allow the cured resin to be fitted over said teeth.

2. The method according to claim 1 wherein said resin precursor is applied to opposite sides of said substrate and both upper and lower teeth are moved into contact with said substrate and embedded in said mixture.

3. The method according to claim 1 including the further step of directing high intensity light against said mixture to enhance curing.

4. The method according to claim 1 wherein said resin precursor and catalyst therefor are applied by simultaneously expelling said resin precursor and catalyst therefor from a double syringe onto said substrate and at least one tooth to form and position said mixture.

5. The method according to claim 4 wherein upper and lower teeth are brought together with the substrate therebetween to clamp said substrate and said mixture is applied to opposite sides of said substrate and to at least one upper tooth and at least one lower tooth.

6. A method of making an occlusally retained mouthpiece which comprises the steps of:

providing a substrate;

providing a two-part resin precursor which is neither caustic nor irritating to teeth or gingival tissue;

said resin precursor selected from the group consisting of precursors for Bisphenol A diglycidyl ether dimethacrylate and urethane dimethacrylate resins and mixtures thereof;

inserting said substrate into a patient's mouth into contact with at least one tooth;

applying a quantity of a mixture comprising said resin precursor to said substrate and said at least one tooth;

partially curing said resin precursor to a shape retaining state;

removing said substrate from said patient's mouth;

fully curing said resin to a tough, flexible state bonded to said substrate; and removing any excess resin from interproximal and undercut areas to allow the cured resin to be fitted over said teeth.

7. The method according to claim 6 wherein said resin is partially cured and fully cured by directing light of predetermined wavelengths against said resin.

8. The method according to claim 6 wherein said resin precursor and catalyst therefor are applied by simultaneously expelling said resin precursor and catalyst therefor from a double syringe onto said substrate and at least one tooth to form and emplace said mixture.

9. The method according to claim 6 wherein upper and lower teeth are brought together with the substrate therebetween to clamp said substrate and said mixture is applied to opposite sides of said substrate and to at least one upper tooth and at least one lower tooth.

10. The method according to claim 6 wherein said mixture is applied to a surface of a substrate and said substrate is pressed against at least one tooth to embed said tooth in said mixture.

11. The method according to claim 6 wherein said substrate is formed from the same resin precursor as is applied to said substrate.

12. A dental mouthpiece which comprises:

a substrate;

a layer of impression material on said substrate, said material comprising a resin which is neither caustic nor irritating to teeth or gingival tissue;

said substrate formed from a resin selected from the group consisting of Bisphenol A dialycidyl ether dimethacrylate and urethane dimethacrylate resins and mixtures thereof;

said resin being selected from the group consisting of precursors for Bisphenol A diglycidyl ether dimethacrylate and urethane dimethacrylate resins and mixtures thereof;

said layer bearing an impression of at least one tooth; and said resin being cured to a tough, flexible state and firmly bonded to said substrate.

13. The dental mouthpiece according to claim 12 wherein said substrate carries a predetermined quantity of said resin on first and second opposite sides and said impression material bears the impression of at least one upper tooth on said first side and at least one lower tooth on said second side.

14. The dental mouthpiece according to claim 12 wherein said substrate is formed from the same material as said impression material.

* * * * *